(12) United States Patent
Yiv et al.

(10) Patent No.: US 6,245,349 B1
(45) Date of Patent: *Jun. 12, 2001

(54) DRUG DELIVERY COMPOSITIONS SUITABLE FOR INTRAVENOUS INJECTION

(75) Inventors: Seang H. Yiv; Alex K. Tustian, both of Wilmington, DE (US)

(73) Assignee: Élan Corporation plc, Dublin (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/606,405

(22) Filed: Feb. 23, 1996

(51) Int. Cl.$^7$ .............................. A61K 9/127; A61K 9/107
(52) U.S. Cl. ...................... 424/450; 424/400; 514/937; 514/393
(58) Field of Search ..................................... 424/450, 400; 514/937, 938, 393

(56) References Cited

U.S. PATENT DOCUMENTS

| | | | |
|---|---|---|---|
| 4,073,943 | 2/1978 | Wretlind et al. | 424/358 |
| 4,146,499 | * 3/1979 | Rosano | 252/186 |
| 4,567,161 | 1/1986 | Posanski et al. | 514/31 |
| 4,719,239 | 1/1988 | Muller et al. | 514/785 |
| 5,002,771 | 3/1991 | Purkaystha | 424/433 |
| 5,023,271 | 6/1991 | Vigne et al. | 514/458 |
| 5,098,606 | 3/1992 | Nakajima et al. | 252/358 |
| 5,110,606 | 5/1992 | Geyer et al. | 424/489 |
| 5,154,930 | 10/1992 | Popescu et al. | 424/489 |
| 5,171,737 | 12/1992 | Weiner et al. | 514/3 |
| 5,188,837 | 2/1993 | Domb | 424/450 |
| 5,206,219 | 4/1993 | Desai | 514/3 |
| 5,227,165 | 7/1993 | Domb et al. | 424/450 |
| 5,340,588 | 8/1994 | Domb | 424/450 |
| 5,395,619 | 3/1995 | Zalipsky et al. | 424/450 |
| 5,444,041 | 8/1995 | Owen et al. | 514/2 |
| 5,478,860 | 12/1995 | Wheeler et al. | 514/449 |
| 5,496,811 | 3/1996 | Aviv et al. | 514/78 |
| 5,741,512 | * 4/1998 | Hauer | 424/450 |

FOREIGN PATENT DOCUMENTS 1171125  11/1969 (GB).

OTHER PUBLICATIONS

M. Debono et al., 1993, ICAAC Abstract No. 359.
W. Turner et al., 1993 ICAAC Abstract No. 358.
Charman et al., *Self–Emulsifying Drug Delivery Systems: Formulation and Biopharmaceutic Evaluation of an Investigational Lipophilic Compound*, Pharmaceutical Research 9, (Jan. 1992), pp. 87–93.

* cited by examiner

Primary Examiner—Gollamudi S. Kishore
(74) Attorney, Agent, or Firm—Synnestvedt & Lechner LLP (57) ABSTRACT

The present invention provides drug delivery compositions in both concentrated and diluted forms for use as vehicles in the administration of various active agents. The drug delivery compositions are primarily designed for use with lipophilic, amphipathic, and sparingly water soluble active agents, preferably drugs. The drug delivery compositions are to be administered to an animal to effect uptake of the active agent. The primary mode of administration is by intravenous, intra-arterial, intrathecal, intraperitoneal, intraocular, intra-articular, intramuscular or subcutaneous injection. The concentrated drug delivery compositions are formulated with a phospholipid component, a component selected from propylene glycol or certain polyethylene glycol compounds, a high HLB surfactant, and the drug component, with water and/or an oil component optional. The concentrated drug delivery compositions can be diluted with an aqueous fluid to form an oil-in-water microemulsion composition.

42 Claims, 1 Drawing Sheet

FIGURE 1

DRUG DELIVERY COMPOSITIONS SUITABLE FOR INTRAVENOUS INJECTION

FIELD OF THE INVENTION

The present invention relates to drug delivery compositions useful for the administration of lipophilic and amphipathic drugs. More specifically, the drug delivery compositions are characterized as being lipid nanoparticles that are stable upon storage and also upon dilution in aqueous buffer.

BACKGROUND OF THE INVENTION

The formulation of lipophilic, amphipathic, or sparingly water soluble drugs into parenteral and pulmonary dosage forms has proven to be difficult. Successful drug delivery vehicles must be capable of maintaining the drug in its dissolved state over an extended storage period. It is also important that the drug delivery vehicle itself remain stable over the storage period.

Commonly employed delivery vehicles for such drugs include liposome and liposphere compositions. Exemplary of such systems are those drug delivery vehicles set forth in U.S. Pat. Nos. 5,395,619, 5,340,588, and 5,154,930. However, these systems suffer from serious drawbacks. As noted in U.S. Pat. No. 5,395,619, liposome compositions are rapidly cleared from the bloodstream, and various modifications to the liposome systems have been proposed to remedy this problem such as formulating with ganglioside $G_{M1}$, coating with polyethylene glycol chains, or attaching polymer compounds to the phospholipid.

Lipid emulsions have also been proposed as alternative delivery vehicles for such drugs. However, the emulsion particle size, generally ranging from about 200 to 1,000 nm, cause these compositions to be readily removed from the blood stream where they tend to accumulate predominately in the liver and spleen. The particle size of the lipid emulsions also precludes the use of filters to sterilize the compositions, thus heat sterilization must be used, which is detrimental to various drugs. From a manufacturing standpoint, lipid emulsions are not preferred due to the requirement of high shear equipment.

Amphipathic drugs containing both hydrophilic and hydrophobic moieties in their structures are frequently poorly soluble in pharmaceutically acceptable oils or aqueous buffers and therefore require administration in potentially irritating compositions containing alcohols or alcohol/surfactant mixtures.

Microemulsions have also been proposed as drug delivery compositions. Microemulsions are generally defined as those systems containing a lipophilic and a hydrophilic component wherein the average particle size of the dispersed phase is below about 150 nm. Microemulsions are further characterized as being clear or translucent solutions. The clarity and particle size characteristics distinguish microemulsions from emulsions. The smaller particle size range of microemulsions enables them to be retained in the blood system for a longer period of time than emulsions. However, microemulsions are generally not dilutable with aqueous fluids, such as certain bodily fluids and buffer solutions, and form emulsions upon contacting such fluids. Various microemulsions are also sensitive to temperature and are not stable outside of room temperature conditions.

A need therefore exists in the art of drug delivery to develop a vehicle that can be used with lipophilic and amphipathic materials and that can be stored at various temperatures for extended periods of time and that can be filter sterilized. The vehicle should also be dilutable with an aqueous fluid such as blood or a buffer solution and still retain these characteristics.

SUMMARY OF THE INVENTION

The present invention provides drug delivery compositions in both concentrated and diluted forms for use as vehicles in the administration of various active agents. The drug delivery compositions are primarily designed for use with lipophilic, amphipathic, and sparingly water soluble active agents, preferably drugs. The drug delivery compositions are to be administered to an animal to effect uptake of the active agent. The primary mode of administration is by intravenous, intra-arterial, intrathecal, intraperitoneal, intraocular, intra-articular, intramuscular or subcutaneous injection. The preferred routes are intravenous, intrathecal or intra-arterial injection. The most preferred routes are intravenous or intra-arterial injection.

The concentrated drug delivery compositions can be formulated with or without an oil component. If present, the oil component can constitute up to about 50 percent by weight of the concentrated composition. The concentrated delivery compositions contain between 3 and 50 percent by weight phospholipid, between 3 and 50 percent by weight of a compound selected from the group consisting of propylene glycol and polyethylene glycol having a weight average molecular weight of from 200 to 4000, and mixtures thereof, and between 3 and 50 percent by weight of a high HLB surfactant having an HLB value of at least about 12. The concentrated compositions contain an active agent, preferably a drug, in an amount of from about 0.1 to about 50 percent by weight. The concentrated compositions can also contain an aqueous component, generally water or a buffer solution, in an amount up to about 15 percent by weight.

Standard pharmaceutical preservatives may be added to either the concentrate or the diluted microemulsion formulations. These may include antioxidants, such as a-tocopherol or ascorbate, and antimicrobials, such as parabens, chlorobutanol or phenol. The preservatives are generally present in an amount of from about 0.1–0.3% by weight.

The concentrated drug delivery compositions can be stored at various temperatures while retaining the active material in its active state. It is preferred, however, to conduct the storage of the delivery composition in its diluted form. The diluted form is prepared by adding an aqueous liquid, preferably water or a buffer solution, to the concentrated composition. The diluted oil-in-water microemulsions form spontaneously, without the need for high shear mixing equipment, upon the addition of the aqueous liquid to the concentrated compositions. The final water content of the diluted composition is at least about 80 percent by weight. The diluted composition can contain between 0.1 and 10 percent by weight phospholipid, between 0.1 and 15 percent by weight of a compound selected from the group consisting of propylene glycol and polyethylene glycol having a weight average molecular weight of from 200 to 4000, and mixtures thereof, between 0.1 and 10 percent by weight of a high HLB surfactant having an HLB value of at least about 12, and an active agent, preferably a drug, in an amount of from about 0.01 to about 5 percent by weight. If present, the oil component can constitute from about 0.1 to about 10 percent by weight of the diluted composition.

The diluted drug delivery compositions are characterized as being nanoparticle compositions. The number average particle size of these compositions is below about 100 nm.

These compositions are also characterized as generally being clear or translucent. These compositions can be stored at freezing conditions, refrigeration conditions, room temperature conditions, and at elevated temperature conditions without concomitant loss of their particle size characteristics. These compositions can be heat or filter sterilized.

The present invention also provides for the administration of the diluted drug delivery composition to an animal to effect administration of the active agent. Modes of administration include intra-arterial, intrathecal, intraperitoneal, intraocular, intra-articular, intramuscular or subcutaneous injection. The preferred routes are intravenous, intrathecal or intra-arterial injection. The most preferred routes are intravenous or intra-arterial injection. The present invention further provides for methods of preparing the diluted drug delivery compositions by the disclosed path dependency sequence.

A benefit of the compositions of the present invention is that the concentrated compositions can be transformed into the diluted oil-in-water microemulsion compositions without the need for high shear mixing equipment. As such, the concentrated compositions can be stored and subsequently diluted with a saline or a buffer solution at the point of use without the need for special mixing equipment. Thus, the concentrated compositions can be transformed into the diluted compositions at any convenient location, such as at a physician's office, at a pharmacy, or in the home.

DETAILED DESCRIPTION OF THE INVENTION

The present invention provides for drug delivery compositions that are suitable for the preferred intravenous and intra-arterial administration modes. The compositions contain the active agent, generally a therapeutic drug compound, dissolved within the components of the composition. The compositions are characterized by having a relatively small particle size in their diluted forms so that the compositions can be filter sterilized. The compositions are stable in their diluted forms, and can thus be stored at refrigerated or freezing temperatures without concomitant loss of active agent activity or drug delivery composition performance. The present invention also provides methods for preparing the drug delivery compositions, and methods for administering the drug delivery compositions to an animal.

The drug delivery compositions of the present invention are specifically adapted for use with active agents, referred to herein also as "drugs." The active agents suitable for use in this invention are either lipophilic or amphipathic. Lipophilic active agents are those materials that have an octanol:water partition coefficient (at room temperature, generally about 23° C.) of greater than 10:1, more preferably greater than 50:1, and even more preferably greater than 100:1. Examples include steroids, benzodiazepines, such as diazepam, carmustine (BCNU), paclitaxel (available as Taxol® from Bristol-Myers Squibb Oncology), and the like. Amphipathic materials may not be soluble in octanol or water to any significant extent. If they are somewhat water soluble, their solubility should be low enough that the volume of aqueous buffer needed to administer an efficacious amount of drug intravenously should be greater than about 1 mL/Kg body weight, or about 1 00 mL for a 70 Kg adult human. Amphipathic materials useful in the present invention are soluble in polar organic solvents such as chloroform, ethylacetate, $C_{1-3}$ alcohols, or dimethyl formamide (DMF), and have a relative solubility in any one of these solvents compared to water of at least 5:1, preferably at least 10:1, and more preferably at least 50:1. Examples include such drugs as cyclosporine (available as Sandimmune® from Sandoz Pharmaceuticals), amphotericin B (available as Fungizone® from Apothecon), tacrolimus, etoposide, teniposide and antifungal echinocandins and azoles, such as clotrimazole and itaconazole.

The drug delivery compositions can be formulated and stored in a concentrated form. The concentrated forms contain a phospholipid material, a high HLB surfactant, a component, such as propylene glycol, polyethylene glycols, and mixtures thereof, useful for aiding in the dispersion of the concentrate in an aqueous buffer and the active agent. For purposes of simplification, the invention will be described with respect to the use of propylene glycol, which is the preferred solubilization component, to represent all such materials. The concentrated forms can optionally contain an oil component. The concentrated forms can also optionally contain a minor amount of water or an aqueous buffer solution suitable for administration purposes.

The concentrated drug delivery compositions can be stored as formulated or with the addition of a major amount of an aqueous phase, generally water or an aqueous buffer solution suitable for administration purposes. The addition of the aqueous phase to the concentrated drug delivery compositions results in the formation of the diluted drug delivery composition. In cases where the concentrated drug delivery system is very viscous at room temperature, such as when the concentration of drug exceeds about 5% by weight, it may be necessary to warm the composition to about 50° C. to 70° C. to liquify the concentrate enough that it will mix readily with the aqueous diluent.

The diluted drug delivery compositions of the present invention can be referred to as oil-in-water (o/w) microemulsions. These o/w microemulsions are characterized by their small particle size, by their wide range of temperature stability, typically from about −20° C. to about 50° C., and they appear to be thermodynamically stable, i.e., stable for extended periods of time at storage conditions. For instance, the microemulsions can be stored at room temperature, e.g. about 22° C., for at least one week, preferably at least one month, and more preferably at least about two months, without evidence of phase separation. These microemulsions also form spontaneously, that is, without the need for high shear mixing of the components. The dispersed internal phase of the o/w microemulsions is constituted by the oil component, if present, and the active agent. Such compositions are also referred to as swollen micellar solutions, although the term o/w microemulsion is used herein. The diluted compositions are characterized as being clear or translucent compositions, which are properties generally associated with microemulsions and swollen micelle solutions. The diluted compositions are thus distinct from liposomes, which have a dispersed, internal aqueous phase, although the diluted compositions of the present invention may contain up to about 5, preferably less than about 2, percent by weight liposomes.

The particle size distribution of the dispersed phase in the diluted drug delivery compositions is such that the compositions are readily filter sterilizable. Filter sterilization is generally conducted by passing the composition through a 0.22 μm sterile filter. The diluted compositions have a number average particle size below about 100 nm, preferably below about 75 nm, more preferably below about 65 nm, and in some cases below about 50 nm. The diluted compositions that do not contain an oil component generally result in the formation of smaller particle size compositions that commonly have number average particle sizes of below about 50 nm and in some cases below about 10 nm. The particle size distribution of the diluted compositions is such that at least 90 percent by weight of the compositions have a number average particle size below about 200 nm, preferably below about 150 nm, and more preferably below about 125 nm, and in the case where no oil components are present this value is below about 75 nm, and preferably below about 50 nm. The particle size determinations can be made by laser light scattering techniques. The diluted drug delivery compositions can be further diluted with an aqueous liquid, such as water or blood, while retaining their nanoparticle size. The diluted compositions are referred to herein as o/w microemulsions because there is a dispersed lipid (oil) phase within a continuous aqueous (water) phase. The lipid phase is primarily the active agent when an oil component is not used, and is the active agent and oil component when an oil component is used. These compositions can also be referred to as nanoparticle solutions, however the term microemulsion is considered more appropriate in view of the limitation on the upper end of the particle size range.

The drug delivery compositions are prepared in the sequence of the concentrated composition first, and then the diluted composition, to ensure optimum solubility of the active agent and to obtain the preferred particle size distribution after dilution with the aqueous liquid. It has been found that the active agent must be blended with the other concentrated drug delivery composition components prior to the dilution with aqueous liquid to achieve superior solubility of the drug in the final, diluted composition. Addition of the drug either simultaneously with, or after, the addition of the aqueous liquid in the amount necessary for forming the diluted composition has been observed to lead to results inconsistent with the described diluted drug compositions of the present invention. Thus, concentrated compositions can be prepared by first blending together, in any order, the phospholipid, high HLB surfactant, propylene glycol, active agent components, and optionally oil and minor amount of water components. The concentrates can then be diluted by the addition of the aqueous liquid to form the diluted compositions.

The phospholipid component of the present invention is a phosphorylated diacylglyceride molecule or derivatives thereof. The parent compound is diacylglycerol phosphate, or phosphatidic acid. Phospholipids include such compounds as phosphatidyl choline, lecithin, which is the choline ester of phosphorylated diacylglyceride, phosphatidylethanolamine, phosphatidylglycerol, phosphatidic acid, and phosphatidylinositol. The acyl chain lengths in the phospholipid molecules are typically between about 4 to 22 carbon atoms, and more generally from about 10 to about 18, having varying degrees of saturation. The phospholipids can be of either natural or synthetic origin. Naturally occurring lecithin can be obtained from a variety of sources such as egg and soya bean. The phospholipid should be acceptable for the chosen route of administration. Useful phospholipids are those surfactants having an HLB value of from about 3 to about 11, preferably from about 3 to about 8. The phospholipid component of the drug delivery compositions can be either a single phospholipid or a mixture of several phospholipids. Commercially available soya phospholipids are the Centrophase and Centrolex products sold by Central Soya and Phospholipon from American Lecithin Co. or Rhone Poulenc Rorer (Germany).

The high HLB surfactants useful in the drug delivery compositions generally have an HLB value of at least 12 and more preferably at least about 15. These surfactants are characterized as having predominantly hydrophilic properties. The preferred surfactants are nonionic and are acceptable for the chosen route of administration. Such high HLB surfactants are known to those of skill in the art. Preferred surfactants found useful in the present invention are the $C_{20-130}$ sorbitol and sorbitan monoesters, diesters, and triesters, and polyoxyethylene (POE) derivatives thereof having 1 to 90 POE groups, e.g., polyoxyethylene sorbitan monooleate and sorbitol hexaoleate POE (50). Other high HLB surfactants that have been used for intravenous drug formulations include: poloxamers, such as Pluronic F68; ethoxylated castor oils, such as Cremophor EL; bile salts, such as deoxycholic acid; and $C_{8-18}$ fatty acid salts, such as sodium oleate. The high HLB surfactant component of the drug delivery compositions can be either a single surfactant or a mixture of several surfactants. Examples of commercially available high HLB surfactants are the Tween series of sorbitol esters available from ICI Americas, Spectrum Chemicals or Sigma Corporation, the Pluronic series of poloxamers available from BASF and the Cremophor series of ethoxylated castor oils, also available from BASF. Other examples of surfactants that may be suitable for use in the compositions include polyoxyethylene esters of fatty acids with HLB values greater than about 15, such as MYRJ 59, polyoxyethylene (100) stearate, HLB 18.8, or MYRJ 52, polyoxyethylene (40) stearate, HLB 16.9, both available from ICI Americas, Inc., Wilmington, Del., or Poly (ethylene glycol) (PEG) derivatives of phosolipids, such as PEG phosphatidyl ethanol amine.

The oil component, if present, is generally a lipophilic material that is preferably a triglyceride or propylene glycol diester oil, or a combination of both of either natural or synthetic origin. Examples of suitable oils for purposes of this invention include triesters of glycerol with fatty acids having 6 to 14, preferably 8 to 12, carbon atoms, and vegetable oils, such as soybean oil, corn oil, poppy seed oil and the like, which are generally liquid at body temperatures, e.g. about 37° C., and mixtures thereof. Suitable oils further include diesters of propylene glycol having from about 7 to 55, preferably 15–27 carbon atoms, most preferably propylene glycol esters of capric and caprylic acids having from 19 to 23 carbon atoms. The triglycerides can be defined as short chain triglycerides having 9–15 carbon atoms, medium chain triglycerides having 21–45 carbon atoms, and long chain triglycerides having above 45 carbon atoms. The long chain triglycerides may be further subdivided into saturated, mono-unsaturated and polyunsaturated triglycerides, depending on whether the fatty acyl moieties of the triglyceride contain no, one, or more than one, double carbon-carbon bond. Mono or polyunsaturated long chain triglycerides, short chain and medium chain triglycerides, preferably short or medium chain, and more preferably medium chain triglycerides are preferred for the present invention. The diesters of propylene glycol are further defined as short chain having from 7–11 carbon atoms, medium chain having from 15–31 carbon atoms, and long chain having above 31 carbon atoms. Examples of glycerol triesters include natural, edible oils such as canola, corn, olive, sunflower and coconut oils, triacetin, the decanoic acid esters, and chemically-synthesized oils such as 1-oleyl-2,3-diacetyl glycerol. Diesters of propylene glycols include propylene glycol esters of capric and caprylic acids, such as Captex 200® (Karlshamns Lipid Specialties, Columbus, Ohio) and other ester groups as described above for glycerol.

As stated previously, the propylene glycol component can be replaced either partially or fully with polyethylene glycol (PEG) compounds. The PEG compounds suitable generally have a weight average molecular weight of from about 100 to about 4000, preferably from about 200 to about 1000, more preferably from about 200 to about 400. Lower primary alcohols, such as ethanol, can be used to form the concentrated compositions; however, such alcohols are not preferred since they are disfavored for intravenous administration.

The phospholipid is present in the concentrated drug delivery compositions in an amount of from about 3 to about 50, preferably from about 10 to about 40, and more preferably from about 15 to about 35, percent by weight. The high HLB surfactant is present in the concentrated drug delivery compositions in an amount of from about 3 to about 50, preferably from about 10 to about 40, and more preferably from about 15 to about 35, percent by weight. The propylene glycol and/or PEG component is present in the concentrated drug delivery compositions in an amount of from about 3 to about 50, preferably from about 5 to about 35, and more preferably from about 10 to about 25, percent by weight. The oil component, if present, will be present in the concentrated drug delivery compositions in an amount of from about 0.5 to about 50, preferably from about 5 to about 40, and more preferably from about 15 to about 40, percent by weight. The water or aqueous buffer solution, if used, will be present in the concentrated drug delivery compositions in an amount of from about 0.01 to about 15, preferably from about 0.01 to about 10, and more preferably from about 0.1 to about 7.5, percent by weight. It is preferred to maintain the weight ratio of the phospholipid to high HLB surfactant below about 3.5:1, preferably in the range of from about 0.1:1 to about 3.0:1, and more preferably from about 0.2:1 to about 2.5:1, and the weight ratio of the phospholipid to the combination of the high HLB surfactant and propylene glycol components to below about 1.5:1, preferably in the range of from about 0.025:1 to about 1.0:1 to produce the o/w microemulsion diluted composition. It is also preferred to maintain the weight ratio of oil to the sum of the phospholipid and high HLB surfactant below 2:1, preferably below 1.5:1, more preferably below 1:1, and in some cases below about 3:7.

The active agent, or drug, can be present in the concentrated drug delivery composition in an amount of from about 0.1 to about 50, preferably from about 0.5 to about 40, and more preferably from about 1 to about 30, percent by weight. The active agent is generally present in the compositions in an efficacious quantity based on the diluted drug composition. This amount will vary depending on the specific active agent chosen.

The concentrated drug delivery compositions are useful for the storage of active agents prior to administration of the active agents to the body of an animal, such as a human. The concentrated compositions are specially designed for storing active agents that are administered by means of intravenous injection. The intravenous mode of administration requires that the delivery composition be sterilized prior to the administration step. The concentrated delivery compositions can be subjected to either heat or filter sterilization, although due to the viscosity of the concentrated forms, heat sterilization is preferable. The concentrated drug delivery compositions can be stored at various temperatures such as freezing conditions, below about 0° C., to as low as about −50° C., refrigerated conditions generally between about 0° C. and about 15° C., room temperature conditions generally between about 15° C. and about 28° C., and elevated conditions as high as about 40° C.

The concentrated drug delivery compositions can be diluted with water or aqueous buffer solutions or dosed directly subcutaneously or intramuscularly to form delivery compositions having an average particle size in the nanometer range. The diluted delivery compositions can then be filter or heat sterilized prior to use, preferably filter sterilized, without significant loss of the active agent.

The drug delivery composition is preferably stored in its diluted form so that the composition is ready for use on demand. However, the concentrated drug delivery composition can also be stored and is then ready for use upon dilution at the time of use. The concentrated drug delivery composition is diluted by adding an aqueous liquid to the concentrated composition. The diluted o/w microemulsions can be formed without the need for high shear mixing equipment, although low shear mixing, such as gentle agitation, is useful, particularly for larger compositions to aid in forming a homogenous composition. This useful property of the claimed compositions has particular benefits—the compositions can be used with drugs that are unstable at high shear conditions, and the concentrated compositions can be used at the point of end use with suitable buffers for treatment of a patient without the requirement for mixing equipment. The aqueous liquid to be added to the concentrated compositions is commonly a buffer solution that is acceptable for intravenous injection such as an phosphate buffer (pH=7–8) or an isotonic saline solution or water. The aqueous liquid is added in an amount such that the aqueous liquid comprises at least about 80, preferably at least about 85, and more preferably at least about 90, percent by weight of the diluted composition. In the general case, with the aqueous liquid being a buffer solution, the weight percent of the aqueous liquid can be considered to be the weight percent of water in the diluted composition. The diluted composition can also be stored at the same temperatures recited for the concentrated composition and subsequently used at room temperature conditions, about 20–25° C., without loss of the nanometer particle size distribution of the internal lipophilic phase and without precipitation of the solubilized active agent.

The phospholipid is present in the diluted drug delivery compositions in an amount of from about 0.1 to about 10, preferably from about 0.5 to about 5, and more preferably from about 0.75 to about 3.5, percent by weight. The high HLB surfactant is present in the diluted drug delivery compositions in an amount of from about 0.1 to about 10, preferably from about 0.5 to about 5, and more preferably from about 0.75 to about 3.5, percent by weight. The propylene glycol and/or PEG component is present in the diluted drug delivery compositions in an amount of from about 0.1 to about 15, preferably from about 0.3 to about 5, and more preferably from about 0.5 to about 3.5, percent by weight. The active agent is present in the diluted drug delivery compositions in an amount of from about 0.05 to about 10, preferably from about 0.1 to about 5, and more preferably from about 0.25 to about 3.5, percent by weight. The oil component, if used, will be present in the diluted drug delivery compositions in an amount of from about 0.1 to about 1 0, preferably from about 0.5 to about 5, and more preferably from about 1 to about 5, percent by weight.

The concentrated and diluted compositions contain the active agent in a solubilized form. The addition of the aqueous liquid to the concentrated drug delivery composition to form the diluted composition does not cause precipitation of the active agent. In general, the concentration of the solubilized active agent in the dispersed phase of the diluted composition will be at least 50, preferably at least about 75, and more preferably at least about 85 percent by weight of the solubilized active agent in the concentrated composition. The concentration of the solubilized active agent in the continuous phase can be determined by UVNIS analysis or by standard HPLC methods after separation of the dispersed phase by ultrafiltration or size exclusion chromatography.

EXAMPLES

All particle size measurements in the following examples were conducted using a laser light scattering technique. The specific instrument used for these examples was a Brookhaven Instruments BI9000 with a 35 mW helium-neon laser.

Example 1

Studies were conducted wherein the path dependency of the preparative technique was shown to exist for the production of a diluted drug delivery composition having the desired particle size. The compositions contained an oil component, Captex 200 (Karlshamns Lipid Specialties), which is a propylene glycol diester oil comprising primarily capric and caprylic acid functionality, a lecithin phospholipid, Centrophase 31 (a liquid lecithin, about 60% wt. lecithin and 40% wt. soybean oil; MW=800; HLB=4.0; Central Soya), a high HLB surfactant, Tween 80 (polyoxyethylene (20) sorbitan monooleate; HLB=15; Sigma Corp.), propylene glycol, and water. The drug utilized was a semisynthetic lipopeptide antifungal agent related to the natural products Echinocandin B's. The natural products have been modified by replacing the lipophilic side chain, linoleic acid, with a modified triphenyl group. Its structure and biological activities have been described as the LY303366 compound in M. Debono et al., 1993, ICAAC Abstract No. 359 and W. Turner et al., 1993, ICAAC Abstract No. 358. These Echinocandin B derivatives have molecular weights between about 800 and about 1600, depending on the degree of modification.

The components were first blended together in the amounts as shown in Table 1.1. The resultant composition was a crude, milky emulsion with an average particle size of 163 nanometers (nm). It was observed that this emulsion contained unsolubilized drug particles.

TABLE 1.1

| Component | Percent By Weight |
| --- | --- |
| Drug | 0.50 |
| Captex 200 | 1.44 |
| Centrophase 31 | 0.90 |
| Tween 80 | 1.26 |
| Propylene Glycol | 0.90 |
| Water | 95.0 |

A second path was used to prepare the drug delivery composition. In this preparation an initial mixture was made in accordance with Table 1.2. The initial mixture was then diluted with water to produce an oil-in-water (o/w) microemulsion by the addition of 19 parts water to one part of the initial mixture. The drug was then added in an amount of 0.005 parts drug to one part of the o/w microemulsion. The resultant composition was determined to have an average particle size of about 41 nm, however drug crystals were visible.

TABLE 1.2

| Component | Percent By Weight |
| --- | --- |
| Captex 200 | 32.0 |
| Centrophase 31 | 20.0 |
| Tween 80 | 28.0 |
| Propylene Glycol | 20.0 |

A third path was used to prepare the drug delivery composition. In this preparation an initial mixture was made in accordance with Table 1.3, however the drug was not added until the other components were admixed together to form an initial homogeneous solution. The drug was then added and the contents stirred until the drug was dissolved. This solution was then diluted with water in an amount of 19 parts water to one part solution to form an oil-in-water microemulsion with an average particle size of about 10 nm, with no evidence of drug crystals. This resultant o/w microemulsion can be further diluted with water while retaining its particle size and it can be easily filter sterilized through a 0.22 $\mu$m filter.

TABLE 1.3

| Component | Percent By Weight |
| --- | --- |
| Drug | 10.0 |
| Captex 200 | 28.8 |
| Centrophase 31 | 18.0 |
| Tween 80 | 25.2 |
| Propylene Glycol | 18.0 |

A portion of the composition prepared by the third path was frozen for 21 days at −20° C., and subsequently thawed at room temperature, about 22° C. Visual inspection indicated that there was no evidence of phase separation, no apparent change in particle size as judged by visual inspection, and no evidence of drug crystallization. This freeze/thaw procedure was repeated three more times, and no evidence of any change in the composition was noticed.

Example 2

Figure 1:
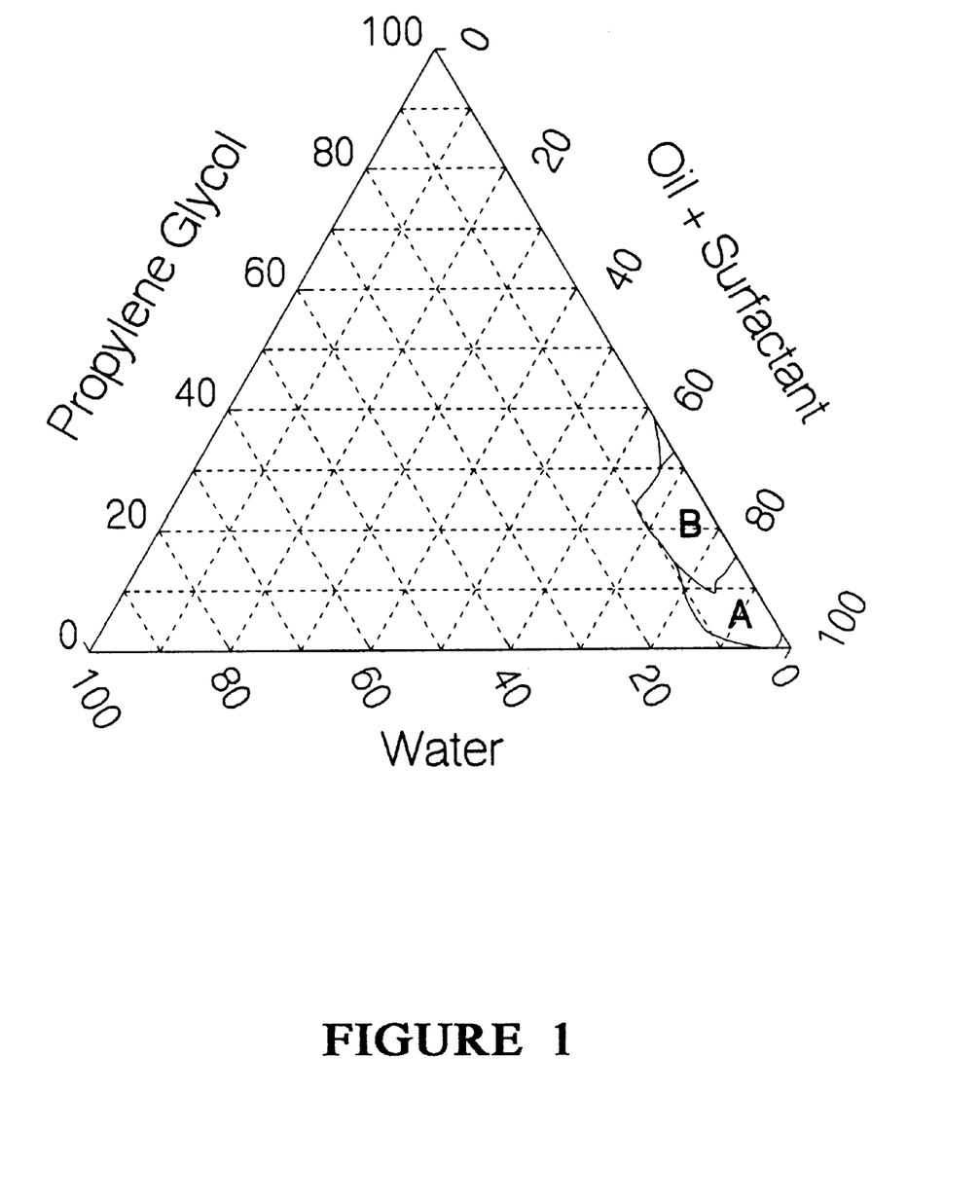
FIG. 1 is a phase diagram wherein the compositions set forth in region B define concentrated drug delivery systems made in accordance with the present invention that can be diluted with water to form the diluted compositions of the present invention.

The path dependency of forming the diluted drug delivery compositions having the desired particle size and stability properties is demonstrated by this example. A phase diagram was developed for systems using the components set forth in Example 1, except the drug was not used to prepare these compositions. The resulting phase diagram is shown in FIG. 1. The (oil+surfactant) component was constituted by 4 parts Captex 200, 3.5 parts Tween 80, and 2.5 parts Centrophase 31. The regions A and B were both areas that define multi-component systems that do not phase separate. However, only those compositions in region B were found to convert to o/w microemulsions having number average particle sizes below at least 125 nm upon the addition of water in an amount of at least about 4 parts water to 1 part of the initial composition. The compositions in region A were found to convert to o/w emulsions upon the addition of water and had number average particle sizes of greater than about 1 50 nm and were of a milky consistency.

Example 3

The methods of the present invention were used to prepare an injection delivery vehicle for the antifungal azole drug, clotrimazole, available from Spectrum Chemical Mfg. Corp., New Brunswick, N.J.

The final diluted drug delivery formulation is set forth in Table 3.1.

TABLE 3.1

| Component | Concentration (o/o w/w) |
|---|---|
| Clotrimazole | 0.4 |
| Captex 300 | 4.1 |
| Phospholipon 90 G | 1.2 |
| Tween 80 | 2.9 |
| Propylene Glycol | 1.4 |
| 10 mM Phosphate Buffer, pH = 7.4 | q.s. |

The diluted formulation was prepared by mixing Captex 300 (glycerol tricaprylate/caprateoil available from Karlshamns Lipid Specialties), Phospholipon 90G (solid phosphatidylcholine purified from soya lecithin, containing ca. 85% unsaturated fatty acids, HLB=7), Tween 80, and propylene glycol together to an initial solution. The clotrimazole was then added and the solution was heated to about 60° C. with stirring by means of a magnetic stir bar for about 15 minutes after which the clotrimazole was completely dissolved as determined by visual inspection. The solution was then diluted with the phosphate buffer to produce the final formulation that was a translucent nanoparticle solution.

The formulation was filtered through a 0.22 micron filter with no change in appearance. The filtered formulation showed no evidence of precipitation or phase separation after four weeks storage at room temperature (23° C.).

Example 4

The methods of the present invention were used to prepare injection delivery vehicles for the antiinflammatory steroid drug, hydrocortisone (available from Spectrum Chemical, New Brunswick, N.J).

The final diluted drug delivery formulation is set forth in Table 4.1.

TABLE 4.1

| Component | Concentration (% w/v) |
|---|---|
| Hydrocortisone | 0.1 |
| Captex 300 | 4.2 |
| Phospholipon 90 G | 1.3 |
| Tween 80 | 2.9 |
| Propylene Glycol | 1.5 |
| 10 mM Phosphate Buffer, pH = 7.4 | q.s. |

The diluted formulation was prepared by mixing Captex 300, Phospholipon 90G, Tween 80, and propylene glycol together to an initial solution.

The hydrocortisonewas then added with stirring by means of a magnetic stir bar until the drug was completely dissolved as determined by visual inspection. The solution was then diluted with the phosphate buffer to produce the final formulation that was a translucent nanoparticle solution.

The formulation was filtered through a 0.22 micron filter with no change in appearance. The filtered formulation showed no evidence of precipitation or phase separation after five weeks storage at room temperature (23° C.).

Example 5

A study was conducted to evaluate the stability of the intravenous drug delivery compositions prepared in accordance with the present invention. The active agent utilized was the antifungal compound described in Example 1.

Two inventive formulations, Formulations A and B, were prepared having a concentrated composition as set forth in Table 5.1.

TABLE 5.1

| | Percent by Weight | |
|---|---|---|
| Component | Formulation A | Formulation B |
| Drug | 10.0 | 10.0 |
| Captex 200 | 29.7 | 31.05 |
| Centrophase 31 | 18.55 | 19.4 |
| Tween 80 | 26.0 | 27.17 |
| Propylene Glycol | 15.75 | 12.38 |

Water was admixed to the inventive formulations to form o/w microemulsions. The final compositions are shown in Table 5.2.

TABLE 5.2

| | Percent by Weight | |
|---|---|---|
| Component | Formulation A | Formulation B |
| Drug | 0.55 | 0.55 |
| Captex 200 | 1.62 | 1.70 |
| Centrophase 31 | 1.0 | 1.06 |
| Tween 80 | 1.42 | 1.5 |
| Propylene Glycol | 0.86 | 0.68 |
| Buffer (10 mm phosphate, pH = 7.4) | balance | balance |

The diluted formulations were sterile filtered through a 0.22 $\mu$m Millex GV disposable syringe filter (Millipore) into sterile containers. The concentration of the active agent was 5.46 mg/ml, as determined by UV spectrophotometry, in both formulations.

The formulations A and B were substantially similar in composition, however the resultant o/w microemulsions had different average particle sizes as shown in Table 5.3. The formulations were divided and stored for 4 weeks at various temperatures. The different storage temperatures did not effect the particle size of the compositions.

TABLE 5.3

| | Initial | 4 wks @ 4 C. | 4 wks @ 25 C. | 4 wks @ 30 C. |
|---|---|---|---|---|
| | Formulation A | | | |
| Effective Diameter (nm) | 40.5 | 39.8 | 39.2 | 39.5 |
| pH | 7.20 | 7.23 | 7.18 | 7.15 |
| Osmolarity (millosmoles) | 142 | — | — | — |
| | Formulation B | | | |
| Effective Diameter (nm) | 60.1 | 45.5 | 47.7 | 45.8 |
| pH | 7.20 | 7.2 | 7.15 | 7.13 |
| Osmolarity (millosmoles) | 121 | — | — | — |

Example 6

An antifungal agent, such as either clortrimazole or an Echinocandin B derivative, is tested in the diluted drug delivery composition of the present invention. The active agent is formulated in a concentrated composition in accordance with the procedures set forth in Example 5 for Formulation A. The concentrated composition is then diluted with buffer solution to form a diluted formulation in accordance with the procedures set forth in Example 5 for Formulation A.

The diluted formulation is then administered intravenously through the tail vein to a series of rats. The animals are sacrificed at various time intervals from 10 minutes to two days after dosing. The level of the active agent in the blood, plasma and/or tissue of the animals is determined by extraction (for tissue) and HPLC techniques. The level of the active agent is determined as µg active agent per ml blood or per g tissue.

Example 7

The methods of the present invention were used to prepare an intravenous delivery vehicle for an anticancer agent, paclitaxel, which is a diterpenoid isolated from the Western Yew, taxus brevifolia, available from Seripharm, Le Mans (France).

The concentrate drug delivery formulation is set forth in Table 7.1.

TABLE 7.1

| COMPOUND | WEIGHT PERCENT |
| --- | --- |
| Paclitaxel | 0.60 |
| Phospholipon 90G | 9.80 |
| Tween 80 | 32.44 |
| Captex 300 | 42.25 |
| PEG 200 | 14.91 |

The diluted formulation was prepared by mixing Captex 300, Phospholipon 90G, Tween 80, and. PEG 200 (Mw= 199, high purity; Spectrum Chemicals) together to form an initial lipid concentrate solution. The paclitaxel was then added with stirring by means of a magnetic stir bar until the drug was completely dissolved as determined by visual inspection. The drug was solubilized by heating it to 60° C. for 15–20 minutes. The concentrate was checked for birefringence by polarized light. No birefringence was observed. The warm concentrate containing 0.6% w/w paclitaxel was then diluted with sterile water for injection to produce the final formulation that had a translucent nanoparticle solution with a number average particle size of about 27–35 nanometers containing 0.06% w/v paclitaxel.

A part of the formulation was filtered through a 0.22 micron filter. The filtered and the unfiltered formulation showed no evidence of phase separation or precipitation after one week storage at room temperature (21±2° C.).

Example 8

A one kilogram batch of drug-free (placebo) formulation and a formulation containing 2% drug were prepared.

As a control for biological evaluation of drug delivery formulations, it was necessary to prepare drug-free, or placebo, formulations for testing in parallel with testing the drug-containing material, in order to separate drug effects from effects of formulation excipients. The following experiment provides a description of the procedures for preparing a placebo and a 2% drug-containing formulation, where the drug used was the Echinocadin B derivative described in Example 1.

A. 10% (w/w) Placebo formulation: The lipid portion of the placebo formulation was prepared in the following manner: 42.5 grams of Captex 300 (triglyceride of medium chain fatty acids primarily capric and caprylic acid) was added to a glass 250 mL beaker followed by the addition of 29.75 grams of Tween 80, 1 5.0 grams of propylene glycol, and 12:75 grams of Phospholipon 90 G. A magnetic stirring bar was added to the beaker and the beaker was placed in a 60° C. water bath on top of a magnetic stirring base. The mixture was stirred until all the phospholipid was dissolved. This required about 40 minutes to 1 hour. In the mean time 600 grams of phosphate buffer (1.9 grams of dibasic sodium phosphate, heptahydrate; 0.2 grams of monobasic sodium phosphate, monohydrate; and 0.9 grams of sodium chloride per liter) was added to a tarred, 2 liter beaker and stirred with a paddle wheel stirrer (Lightning Mixer) and stirred at 700 rpm. After the phospholipid had dissolved, the warm lipid mixture was slowly poured into the vortex of the mixing buffer. The weight of the added lipid was recorded. Once all the lipid phase has been transferred and a homogeneous emulsion formed, additional buffer was added to adjust the final weight of the preparation to the target composition of 10% (w/w) of lipid phase.

B. Preparation of a formulation containing 20 mg/mL final concentration of the Echinocandin B derivative: 40.07 grams of Captex 300, 28.05 grams of Tween 80, 14.15 grams of propylene glycol and 12.02 grams of Phospholipon 90 G were weighed into a tarred 250 ml glass beaker. The lipid mixture was heated and stirred as in Part A until the phospholipid dissolved. Then 20 grams of the drug was added to the warm lipid mixture and the mixture was stirred at temperature until all the drug dissolved (10 to 15 minutes). Meanwhile, 600 grams of buffer was weighed into a 2 liter beaker and stirred as in Part A . The warm, drug-containing lipid concentrate was mixed with the buffer as described above and the mixing continued for 15 mins. Additional buffer was then added and mixed until the estimated drug concentration achieved the target concentration of 20 mg/mL of formulation.

Both formulations were filtered through a 0.22 micron filter and then the particle size was determined by laser light scattering. The placebo formulation and the drug containing formulation both had average particle diameters of less than 55 nm.

Compositions were made containing 10 mg/mL drug and 2 mg/mL drug by diluting the 20 mg/mL stock with physiological saline solution. The diluted compositions were stable and retained the small average particle size seen in the stock 20 mg/mL formulation.

The hemolytic potential of the placebo formulation was tested by mixing various dilutions of the placebo with 5% suspension of dog red blood cells. The mixtures were incubated at 37° C. for 15 minutes. The red cells were pelleted by centrifugation at 100×g for 5 minutes and the supernatant was assayed for released hemoglobin by measuring the absorbance at 430 nm. The per cent hemolysis was calculated by taking the absorbance of the sample, subtracting off the absorbance of the blank cells, treated with physiological saline, dividing by the absorbance of a red cell suspension treated with a equal volume of 1% (w/v) sodium dodecyl sulfate solution, which causes 100% hemolysis, and multiplying by 100%. A mixture of an equal volume of placebo formulation with the red cell suspension caused only about 2.5% hemolysis, which is well within tolerable limits for parenteral products.

The hemolytic potential of the drug formulation can be tested in a similar fashion as the placebo formulation.

Example 9

Studies were conducted in order to demonstrate the utility and necessity of incorporating either propylene glycol (PG)

or polyethylene glycol (PEG) to the concentrated drug delivery formulation to obtain chemically and physically stable microemulsions after inversion with an aqueous phase.

Lipid concentrates were prepared by blending a phospholipid, Phospholipon 90G, and a surfactant, Tween 80, in phospholipid to surfactant molar ratios between 1:1 and 1:2. The weight percents of the components for these lipid concentrate, drug-free mixtures, are in Table 9.1. The concentrates were prepared by mixing all components at a temperature of 60° C. From these heterogeneous mixtures different solutions were prepared by mixing them with 1 5 volume percent of either propylene glycol (>99.5% purity; Spectrum Chemicals) or PEG 200. The resulting solutions were homogeneous and stable. One part of each of these solutions was then heated to 60° C. and diluted with 9 parts of water to produce an o/w microemulsion, which was clear or translucent. Compositions made without the propylene glycol or PEG component were found to produce milky, opaque emulsions upon dilution with water.

TABLE 9.1

|  | Molar Ratio | | |
| --- | --- | --- | --- |
|  | 1:2 | 1:1.4 | 1:1 |
| Component | Weight Percent | | |
| Phospholipon 90G | 11.6 | 15 | 18.8 |
| Tween 80 | 38.4 | 35 | 31.2 |
| Captex 300 | 50.0 | 50 | 50.0 |

Quasielastic light scattering (QELS) measurements were performed in order to obtain the mean droplet size and the size distribution at room temperature (21±2° C.). Each sample was once more diluted with water in order to have in the final solution 1% w/v dispersed phase (oil and surfactants) in water. These samples were filtered through a 0.22 micron sterile filter with no change in appearance, then submitted to centrifugation for one hour at approximately 420×g. In all cases, when there was no propylene glycol or PEG 200, phase separation occurred indicating that these were not thermodynamically stable microemulsions. On the other hand, the solutions containing propylene glycol or PEG 200 remained homogeneous and isotropic. Table 9.2 presents the results obtained for different molar ratios with or without the addition of propylene glycol or PEG 200 when diluted to a final concentration of 1% w/v.

TABLE 9.2

|  | Mean Droplet Size (±5 nm) With (C) and Without Centrifugation (nC) | | |
| --- | --- | --- | --- |
| Molar Ratio | No Additive | With Propylene Gylcol | With PEG 200 |
| 1:2 | 96 (nC) | 33 (C)/84 (nC) | 26 (C)/22 (nC) |
| 1:1.4 | 113 (nC) | 25 (C)/25 (nC) | 39 (C)/31 (nC) |
| 1:1 | 110 (nC) | 32 (nC) | 94 (nC) |

From Table 9.2 and observations made after centrifugation, it is clearly shown that the addition of propylene glycol or PEG 200 to the concentrates results in the creation of smaller droplets (hence clear mixtures) and physically stable solutions after dilution in water.

What is claimed is:

1. A drug delivery composition in concentrate form that contains an antifungal agent and that is dilutable with an aqueous liquid to form an oil-in-water microemulsion containing the antifungal agent in dissolved form, consisting essentially of:

(a) from about 3 to about 50 percent by weight phospholipid;

(b) from about 3 to about 50 percent by weight propylene glycol, polyethylene glycol having a weight average molecular weight of from 200 to 4000, or mixtures thereof;

(c) from about 3 to about 50 percent by weight of high HLB surfactant having an HLB value of at least about 12;

(d) from 0 to about 15 percent by weight water; and (e) from about 0.1 to about 50 percent by weight of dissolved antifungal agent comprising Echinocandin B derivatives, clotrimazole, or mixtures thereof;

wherein the weight ratio of phospholipid to high HLB surfactant is between 0.1:1 and 3:1.

2. The composition of claim 1 wherein the composition comprises from about 3 to about 50 percent by weight propylene glycol.

3. The composition of claim 2 wherein said phospholipid is present in an amount of from 10 to 40 percent by weight, said propylene glycol is present in an amount of from 5 to 35 percent by weight, and said high HLB surfactant is present in an amount of from 10 to 40 percent by weight.

4. The composition of claim 2 wherein the weight ratio of said phospholipid to said high HLB surfactant is from 0.2:1 to 2.5:1.

5. A drug delivery composition in concentrate form that contains an antifungal agent and that is dilutable with an aqueous liquid to form a stable oil-in-water microemulsion containing the antifungal agent in its dissolved form, consisting essentially of:

(a) from about 3 to about 50 percent by weight phospholipid;

(b) from about 3 to about 50 percent by weight propylene glycol, polyethylene glycol having a weight average molecular weight of from 200 to 4000, or mixtures thereof;

(c) from about 3 to about 50 percent by weight of high HLB surfactant having a HLB value of at least about 12;

(d) from about 0.5 to about 50 percent by weight of an oil component;

(e) from 0 to about 15 percent by weight water; and (f) from about 0.1 to about 50 percent by weight of dissolved antifungal agent comprising Echinocandin B derivatives, clotrimazole, or mixtures thereof;

wherein the weight ratio of phospholipid to high HLB surfactant is between 0.1:1 and 3:1.

6. The composition of claim 5 wherein the composition comprises from about 3 to about 50 percent by weight propylene glycol.

7. The composition of claim 6 wherein said oil component comprises triglycerides having from 9 to 83 carbon atoms, propylene glycol diesters having from 15 to 60 carbon atoms, or mixtures thereof.

8. The composition of claim 7 wherein said oil component consists of said triglycerides, propylene glycol diesters, and mixtures thereof.

9. The composition of claim 8 wherein said phospholipid is present in an amount of from 10 to 40 percent by weight, said propylene glycol is present in an amount of from 5 to 35 percent by weight, and said high HLB surfactant is present in an amount of from 10 to 40 percent by weight.

10. The composition of claim 9 wherein the weight ratio of said phospholipid to said high HLB surfactant is from 0.2:1 to 2.5:1.

11. A drug delivery composition in diluted form that contains an antifungal agent and that comprises an oil-in-water microemulsion containing the antifungal agent in its dissolved form, consisting essentially of:
  (a) from about 0.1 to about 10 percent by weight phospholipid;
  (b) from about 0.1 to about 15 percent by weight propylene glycol, polyethylene glycol having a weight average molecular weight of from 200 to 4000, or mixtures thereof;
  (c) from about 0.1 to about 10 percent by weight of high HLB surfactant having a HLB value of at least about 12;
  (d) from about 0.05 to about 10 percent by weight of dissolved antifungal agent comprising Echinocandin B derivatives, clotrimazole, or mixtures thereof; and
  (e) at least about 80 percent by weight aqueous liquid comprising water;
  wherein the weight ratio of phospholipid to high HLB surfactant is between 0.1:1 and 3:1.

12. The composition of claim 11 wherein the composition comprises from about 0.1 to about 15 percent by weight propylene glycol.

13. The composition of claim 12 wherein said phospholipid is present in an amount of from 0.5 to 5 percent by weight, said propylene glycol is present in an amount of from 0.3 to 5 percent by weight, and said high HLB surfactant is present in an amount of from 0.5 to 5 percent by weight.

14. The composition of claim 13 wherein the weight ratio of said phospholipid to said high HLB surfactant is from 0.2:1 to 2.5:1.

15. A drug delivery composition in diluted form that contains an antifungal agent and that comprises an oil-in-water microemulsion containing the antifungal agent in its dissolved form, consisting essentially of:
  (a) from about 0.1 to about 10 percent by weight phospholipid;
  (b) from about 0.1 to about 15 percent by weight propylene glycol, polyethylene glycol having a weight average molecular weight of from 200 to 4000, or mixtures thereof;
  (c) from about 0.1 to about 10 percent by weight of high HLB surfactant having a HLB value of at least about 12;
  (d) from about 0.1 to about 10 percent by weight of an oil component;
  (e) from about 0.05 to about 10 percent by weight of dissolved antifungal agent comprising Echinocandin B derivatives, clotrimazole, or mixtures thereof; and
  (f) at least about 80 percent by weight of an aqueous liquid comprising water;
  wherein the weight ratio of phospholipid to high HLB surfactant is between 0.1:1 and 3:1.

16. The composition of claim 15 wherein the composition comprises from about 0.1 to about 15 percent by weight propylene glycol.

17. The composition of claim 16 wherein said oil component comprises triglycerides having from 9 to 83 carbon atoms, propylene glycol diesters having from 15 to 60 carbon atoms, or mixtures thereof.

18. The composition of claim 17 wherein said oil component consists of said triglycerides, propylene glycol diesters, and mixtures thereof.

19. The composition of claim 16 herein said phospholipid is present in an amount of from 0.5 to 5 percent by weight, said propylene glycol is present in an amount of from 0.3 to 5 percent by weight, and said high HLB surfactant is present in an amount of from 0.5 to 5 percent by weight.

20. A method of administering a drug delivery composition, comprising the steps of:
  providing the drug delivery composition consisting essentially of:
    (a) from about 0.1 to about 10 percent by weight phospholipid;
    (b) from about 0.1 to about 15 percent by weight propylene glycol, polyethylene glycol having a weight average molecular weight of from 200 to 4000, or mixtures thereof;
    (c) from about 0.1 to about 10 percent by weight of high HLB surfactant having a HLB value of at least about 12;
    (d) from about 0.05 to about 10 percent by weight of dissolved antifungal agent comprising Echinocandin B derivatives, clotrimazole, or mixtures thereof; and
    (e) at least about 80 percent by weight aqueous liquid comprising water,
  wherein the weight ratio of phospholipid to high HLB surfactant is between 0.1:1 and 3:1,
  wherein said composition comprises a water-in-oil microemulsion; and
  administering said composition to the body of an animal.

21. The composition of claim 2, wherein the weight ratio of the phospholipid to the combination of the high HLB surfactant and propylene glycol components is from about 0.025:1 to about 1:1.

22. The composition of claim 1, wherein the high HLB surfactant comprises $C_{20\text{-}130}$ sorbitol or sorbitan monoester, diesters, and triesters, polyoxyethylene (POE) derivatives thereof having 1 to 90 POE groups, or ethoxylated castor oils.

23. The composition of claim 9, wherein the weight ratio of the phospholipid to the combination of the high HLB surfactant and propylene glycol components is from about 0.025:1 to about 1:1.

24. The composition of claim 5, wherein the high HLB surfactant comprises $C_{20\text{-}130}$ sorbitol or sorbitan monoester, diesters, and triesters, polyoxyethylene (POE) derivatives thereof having 1 to 90 POE groups, or ethoxylated castor oils.

25. The composition of claim 13, wherein the weight ratio of the phospholipid to the combination of the high HLB surfactant and propylene glycol components is from about 0.025:1 to about 1:1.

26. The composition of claim 11, wherein the high HLB surfactant comprises $C_{20\text{-}130}$ sorbitol or sorbitan monoester, diesters, and triesters, polyoxyethylene (POE) derivatives thereof having 1 to 90 POE groups, or ethoxylated castor oils.

27. The composition of claim 11, wherein the aqueous liquid comprises at least about 90 percent by weight of the drug delivery composition.

28. The composition of claim 19, wherein the weight ratio of the phospholipid to the combination of the high HLB surfactant and propylene glycol components is from about 0.025:1 to about 1:1.

29. The composition of claim 15, wherein the high HLB surfactant comprises $C_{20\text{-}130}$ sorbitol or sorbitan monoester, diesters, and triesters, polyoxyethylene (POE) derivatives thereof having 1 to 90 POE groups, or ethoxylated castor oils.

30. The composition of claim 15, wherein the aqueous liquid comprises at least about 90 percent by weight of the drug delivery composition.

31. The composition of claim 19, wherein the weight ratio of said phospholipid to said high HLB surfactant is from 0.2:1 to 2.5:1.

32. The method of claim 20, wherein said administering step comprises injecting the composition intravenously to the animal.

33. The method of claim 32, wherein the drug delivery composition comprises from about 0.1 to about 15 percent by weight propylene glycol.

34. The method of claim 32, wherein the drug delivery composition contains said phospholipid in an amount of from 0.5 to 5 percent by weight, said propylene glycol is present in an amount of from 0.3 to 5 percent by weight, and said high HLB surfactant is present in an amount of from 0.5 to 5 percent by weight.

35. The method of claim 32, wherein within the drug delivery composition the weight ratio of said phospholipid to said high HLB surfactant is from 0.2:1 to 2.5:1.

36. The method of claim 32, wherein with the drug delivery composition the weight ratio of the phospholipid to the combination of the high HLB surfactant and propylene glycol components is from about 0.025:1 to about 1:1.

37. The method of claim 32, wherein the high HLB surfactant in the drug delivery composition comprises $C_{20-130}$ sorbitol or sorbitan monoester, diesters, and triesters, polyoxyethylene (POE) derivatives thereof having 1 to 90 POE groups, or ethoxylated castor oils.

38. The method of claim 32, wherein the drug delivery composition further comprises from about 0.1 to about 10 percent by weight of an oil component.

39. The method of claim 38, wherein the drug delivery composition comprises from about 0.1 to about 15 percent by weight propylene glycol.

40. The method of claim 39, wherein the drug delivery composition contains said phospholipid in an amount of from 0.5 to 5 percent by weight, said propylene glycol is present in an amount of from 0.3 to 5 percent by weight, and said high HLB surfactant is present in an amount of from 0.5 to 5 percent by weight.

41. The method of claim 39, wherein within the drug delivery composition the weight ratio of said phospholipid to said high HLB surfactant is from 0.2:1 to 2.5:1.

42. The method of claim 38, wherein the high HLB surfactant in the drug delivery composition comprises $C_{20-130}$ sorbitol or sorbitan monoester, diesters, and triesters, polyoxyethylene (POE) derivatives thereof having 1 to 90 POE groups, or ethoxylated castor oils.

* * * * *